United States Patent
Seki (10) Patent No.: US 12,324,088 B2
(45) Date of Patent: Jun. 3, 2025

(54) ION SOURCE, CIRCULAR ACCELERATOR USING SAME, AND PARTICLE BEAM THERAPY SYSTEM

(71) Applicant: Hitachi, Ltd., Tokyo (JP)

(72) Inventor: Takayoshi Seki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1100 days.

(21) Appl. No.: 17/281,626

(22) PCT Filed: Sep. 12, 2019

(86) PCT No.: PCT/JP2019/035916
§ 371 (c)(1),
(2) Date: Mar. 31, 2021

(87) PCT Pub. No.: WO2020/166116
PCT Pub. Date: Aug. 20, 2020

(65) Prior Publication Data
US 2021/0393986 A1  Dec. 23, 2021

(30) Foreign Application Priority Data
Feb. 14, 2019 (JP) .................................. 2019-024347

(51) Int. Cl.
*H05H 7/08* (2006.01)
*A61N 5/10* (2006.01)
(Continued)

(52) U.S. Cl.
CPC ............. *H05H 7/08* (2013.01); *A61N 5/1077* (2013.01); *G21K 1/093* (2013.01); *H05H 1/10* (2013.01);
(Continued)

(58) Field of Classification Search
CPC .......... H05H 7/08; H05H 1/10; H05H 1/4622; H05H 1/54; H05H 13/005;
(Continued)

(56) References Cited

U.S. PATENT DOCUMENTS 8,624,502 B2 * 1/2014 Rosenthal ............... H01J 27/18
315/111.41
9,520,271 B2 * 12/2016 Vandermeulen ........ H01J 37/05
(Continued)

FOREIGN PATENT DOCUMENTS

JP  2011-523185 A  8/2011

OTHER PUBLICATIONS

International Search Report of PCT/JP2019/035916 dated Dec. 10, 2019.

*Primary Examiner* — Renan Luque
(74) *Attorney, Agent, or Firm* — MATTINGLY & MALUR, PC (57) ABSTRACT

The ion source includes a microwave power supply provided outside main magnetic poles, a radiofrequency waveguide and an antenna configured to introduce a microwave generated by the microwave power supply to a region to which a magnetic field generated by the main magnetic poles is applied, and a magnetic field generation unit provided inside a hole provided in a part of the main magnetic poles and configured to generate a magnetic field in a direction opposite to that of the magnetic field generated by the main magnetic poles. Plasma is generated inside the main magnetic poles by a magnetic field generated by applying the magnetic field generated by the magnetic field generation unit in the opposite direction to the main magnetic field decreased according to a diameter of the hole and the microwave introduced by the radiofrequency waveguide and the antenna.

6 Claims, 9 Drawing Sheets

(51) Int. Cl.
  *G21K 1/093* (2006.01)
  *H05H 1/10* (2006.01)
  *H05H 1/46* (2006.01)
  *H05H 1/54* (2006.01)
  *H05H 13/00* (2006.01)

(52) U.S. Cl.
  CPC ............ *H05H 1/4622* (2021.05); *H05H 1/54* (2013.01); *H05H 13/005* (2013.01); *A61N 2005/1087* (2013.01); *H05H 2007/082* (2013.01)

(58) Field of Classification Search
  CPC ............ H05H 2007/082; A61N 5/1077; A61N 2005/1087; G21K 1/093; H01J 27/16; H01J 37/08
  See application file for complete search history.

(56) References Cited

U.S. PATENT DOCUMENTS

2011/0068717 A1    3/2011  Kleeven et al.
2020/0281067 A1*   9/2020  Lundin .................... H05H 1/46

* cited by examiner

ION SOURCE, CIRCULAR ACCELERATOR USING SAME, AND PARTICLE BEAM THERAPY SYSTEM

TECHNICAL FIELD

The present invention relates to an ion source suitable for a circular accelerator, a circular accelerator including the same, and a particle beam therapy system.

BACKGROUND ART

As a background of this technical field, PTL 1 is provided. PTL 1 discloses that "the cyclotron includes a second internal ion source configured to generate particle ions same as the first internal ion source, and the cyclotron is configured to generate energetic particle beams generated by either the first internal ion source or by the second internal ion source, or by both the ion sources simultaneously".

CITATION LIST

Patent Literature

PTL 1: JP-T-2011-523185

SUMMARY OF INVENTION

Technical Problem

In PTL 1 described above, two ion sources of the same type are disposed inside, and a life span is extended by switching and using these ion sources. However, the method described in PTL 1 does not consider extending the life span of each ion source, and the life span is simply doubled by two ion sources.

Therefore, in any case, the life span is determined due to damage of a filament. Further, there are problems that it is not possible to avoid large-scale operations such as disassembling a main magnetic pole for filament replacement and opening the main magnetic pole to atmosphere, and an operation rate of the apparatus is lowered.

Therefore, an object of the invention is to provide an internal ion source having a long life span and not including a filament having a determined life span, a circular accelerator using the same, and a particle beam therapy system.

Solution to Problem

The invention includes a plurality of means for solving the problems, and an example thereof is an ion source used for a circular accelerator including magnetic poles facing to each other and a radiofrequency acceleration electrode. The ion source includes: a microwave emission source provided outside the magnetic poles; a waveguide configured to introduce a microwave emitted from the microwave emission source to a region to which a main magnetic field generated by the magnetic poles is applied; and a magnetic field generation unit provided inside a hole provided in a part of the magnetic poles and configured to generate a magnetic field in a direction opposite to a direction of the magnetic field generated by the magnetic poles. Plasma is generated inside the magnetic poles by a magnetic field generated by applying the magnetic field generated by the magnetic field generation unit in the opposite direction to the main magnetic field decreased according to a diameter of the hole and the microwave introduced by the waveguide.

Advantageous Effect

According to the invention, it is possible to provide an internal ion source having a long life span and not including a filament having a determined life span. Problems, configurations, and effects other than those described above will be further clarified with the following description of embodiments.

DESCRIPTION OF EMBODIMENTS

An embodiment of an ion source, a circular accelerator using the ion source, and a particle beam therapy system according to the invention will be described with reference to FIGS. 1 to 9.

Figure 1:
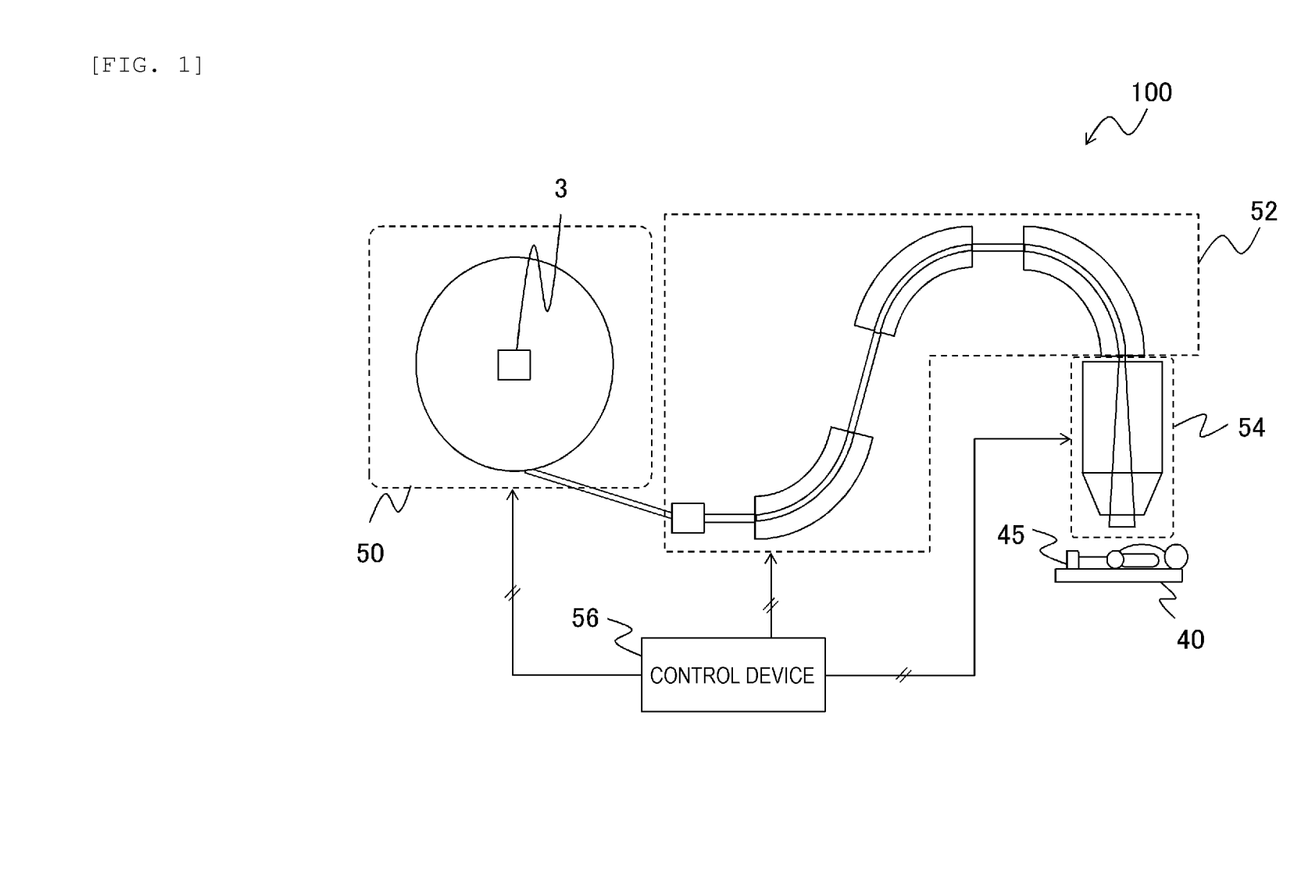
FIG. 1 is a diagram showing an overall configuration of a particle beam therapy system using a circular accelerator of the invention.

First, an overall configuration of the particle beam therapy system and configurations of related devices will be described with reference to FIG. 1. FIG. 1 is a diagram showing the overall configuration of the particle beam therapy system according to the present embodiment.

In FIG. 1, a particle beam therapy system 100 includes a cyclotron accelerator 50, a beam transport system 52, an irradiation nozzle 54, a couch 40, and a control device 56.

In the particle beam therapy system 100, ions generated by an ion source 3 are accelerated by the accelerator 50 to form an ion beam. The accelerated ion beam is emitted from the accelerator 50 and transported to the irradiation nozzle 54 by the beam transport system 52.

The ion beam transported to the irradiation nozzle 54 by the beam transport system 52 is shaped so as to match a target shape, and a target, i.e., a patient 45 lying on the couch 40 is irradiated with a predetermined amount of the ion beam.

Operations of each device and equipment in the particle beam therapy system 100 including the accelerator 50 are controlled by the control device 56.

The control device 56 includes a central processing unit (CPU) and a memory connected to the CPU. The control device 56 reads various operation control programs related to irradiation of each device constituting the particle beam therapy system 100 based on a treatment plan created by a treatment planning apparatus (not shown) and stored in a database (not shown), executes the read programs, and outputs a command, so as to control the operations of each device in the particle beam therapy system 100.

Control processing of the operations to be executed may be integrated into one program, may be divided into a plurality of programs, or may be a combination thereof. A part or all the programs may be implemented by dedicated hardware, or may be modularized. Further, the various programs may be installed by a program distribution server or an external storage medium.

Further, each of the devices may be an independent device connected with each other via a wired or wireless network, or two or more of the devices may be integrated.

Figure 2:
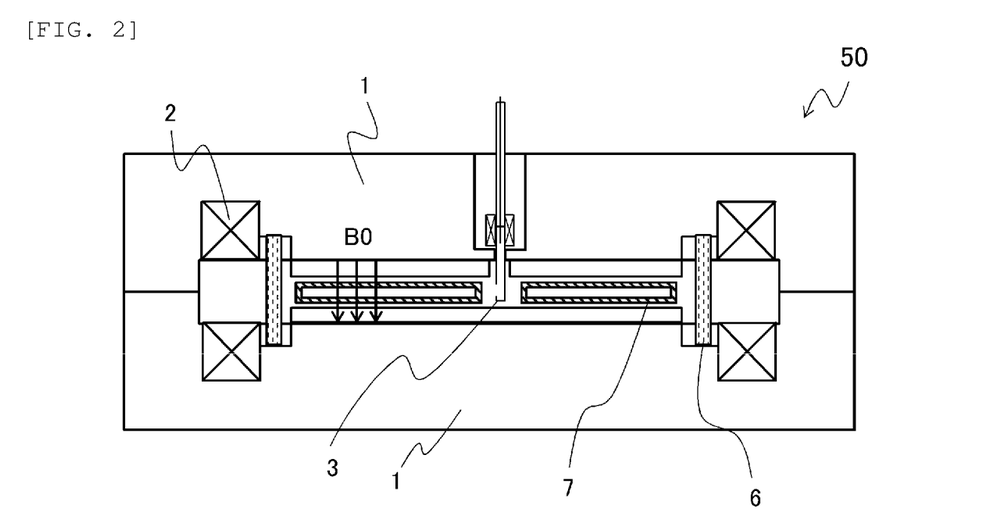
FIG. 2 is a sectional view of a side surface of the circular accelerator shown in FIG. 1.

Next, a structure of the accelerator 50 will be described with reference to FIGS. 2 and 3. FIG. 2 is a sectional view of a side surface of the accelerator of the present embodiment, and FIG. 3 is a cross-sectional view of the accelerator.

Figure 3:
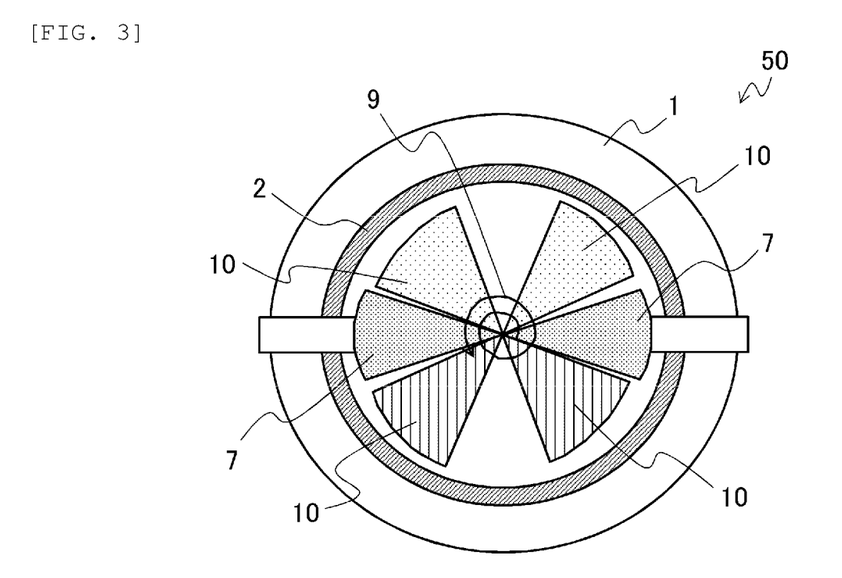
FIG. 3 is a cross-sectional view of the circular accelerator shown in FIG. 1.

As shown in FIGS. 2 and 3, the accelerator 50 includes main magnetic poles 1, an annular coil 2, a vacuum vessel 6, a radiofrequency acceleration electrode 7, and the ion source 3.

The main magnetic poles 1 are a pair of magnetic bodies disposed so as to face each other, and are made of, for example, iron. In the main magnetic poles 1, convex magnetic poles 10 are provided between the magnetic poles facing each other so as to generate a closed orbit 9 of a beam, and an isochronous magnetic field is generated between the magnetic poles. In the accelerator 50, a main magnetic field B0 is generated by the convex magnetic poles 10, and a focusing force of the ion beam circulating in a gradient magnetic field formed by an edge of the convex magnetic poles 10 is increased, thereby contributing to stable circulation. Facing upper and lower surfaces between a magnetic pole gap G generated by the main magnetic field B0 have a symmetrical shape.

The vacuum vessel 6 is sandwiched between the main magnetic poles 1, and forms a single vacuum vessel as a whole and constitutes a magnetic circuit. The vacuum vessel 6 is made of a non-magnetic material. In the magnetic pole gap G, a separate vacuum vessel may be separately provided without using the magnetic pole as an inner surface of the vacuum vessel.

The annular coil 2 is disposed closer to atmosphere than the vacuum vessel 6, and generates a magnetic field same as B0 between the pair of upper and lower main magnetic poles 1. The annular coil 2 can similarly generate a magnetic field regardless of a coil made of a normal conducting material and a coil made of a superconducting material. The annular coil 2 may be provided in the vacuum vessel 6, and is not particularly limited thereto.

Figure 4:
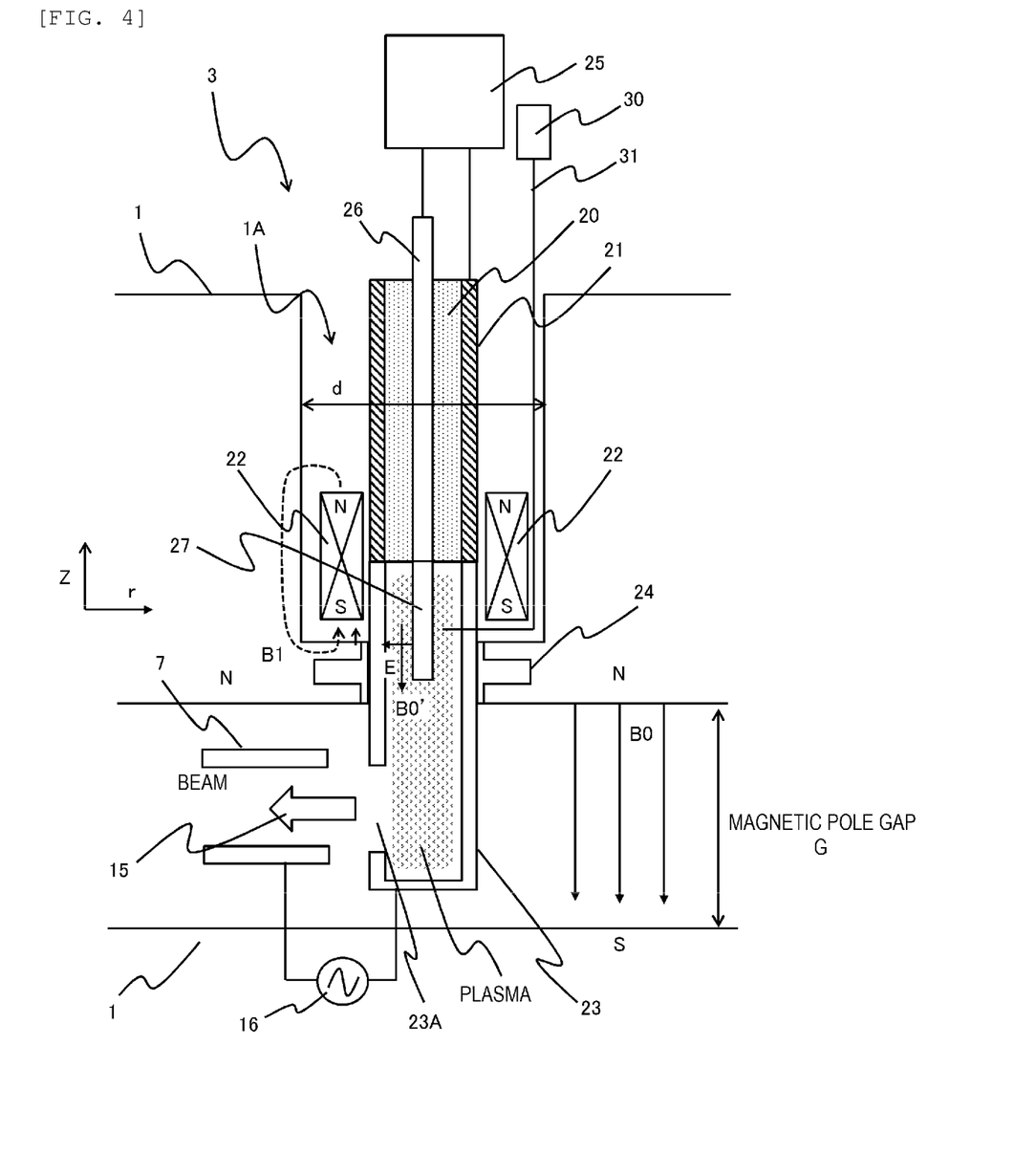
FIG. 4 is a diagram schematically showing a side surface around an ion source in FIG. 1.

The radiofrequency acceleration electrode 7 having a hollow inside is disposed inside the vacuum vessel 6, and a radiofrequency can be applied from outside by a radiofrequency power supply 16 (see FIG. 4).

Next, the ion source 3 will be described in detail with reference to FIGS. 4 to 9.

Figure 5:
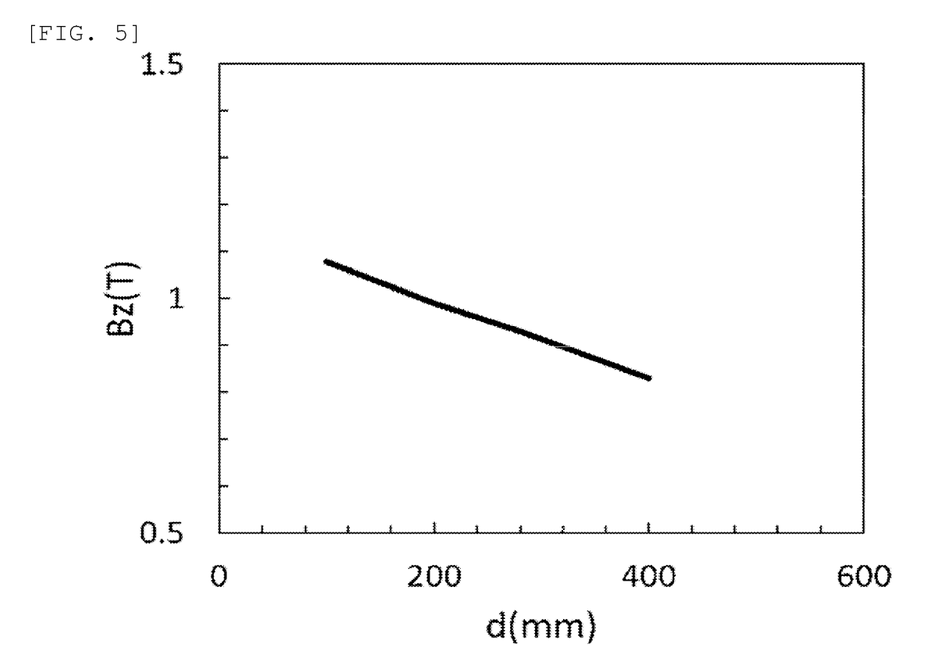
FIG. 5 is a diagram showing a magnetic field intensity when a magnetic pole hole diameter d at a certain position of a center of the ion source in FIG. 4 is changed.
Figure 6:
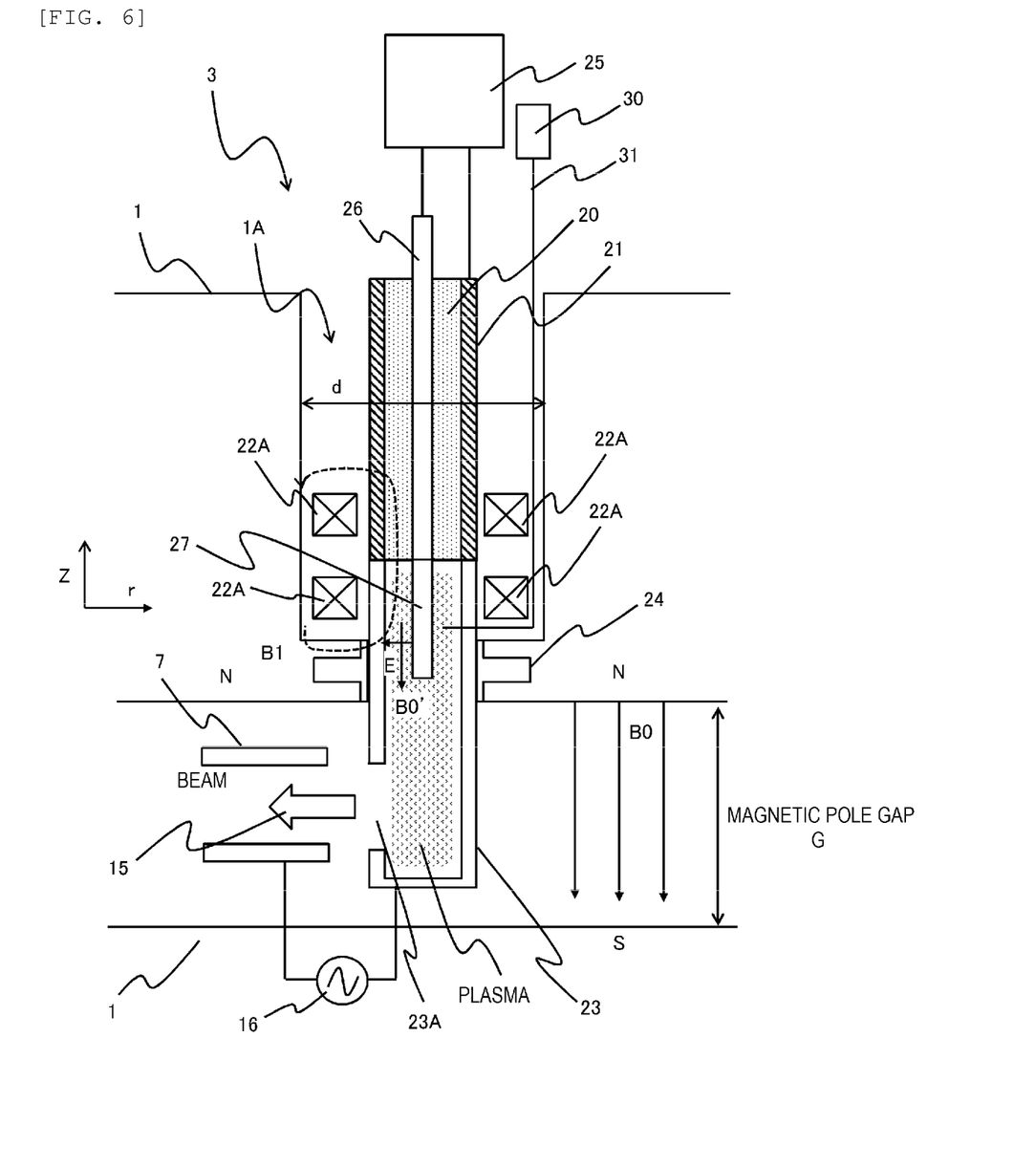
FIG. 6 is a diagram schematically showing another example of the side surface around the ion source in FIG. 1.
Figure 7:
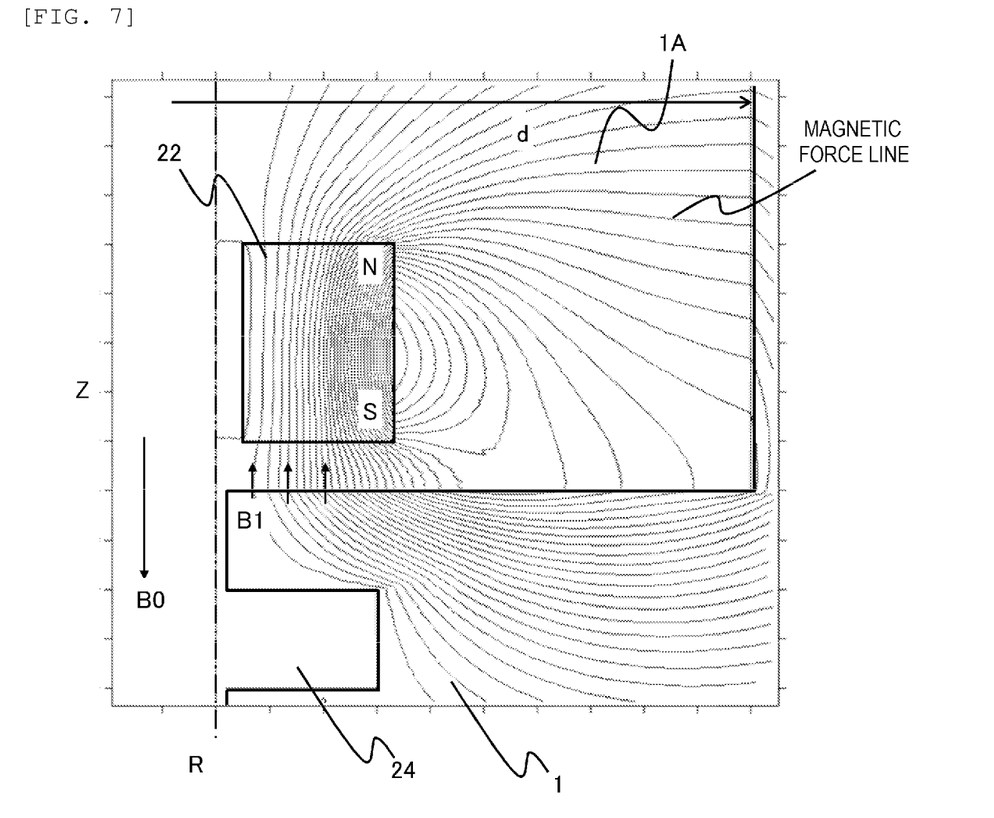
FIG. 7 is a diagram showing magnetic force lines around a magnetic field generation mechanism in FIG. 4.
Figure 8:
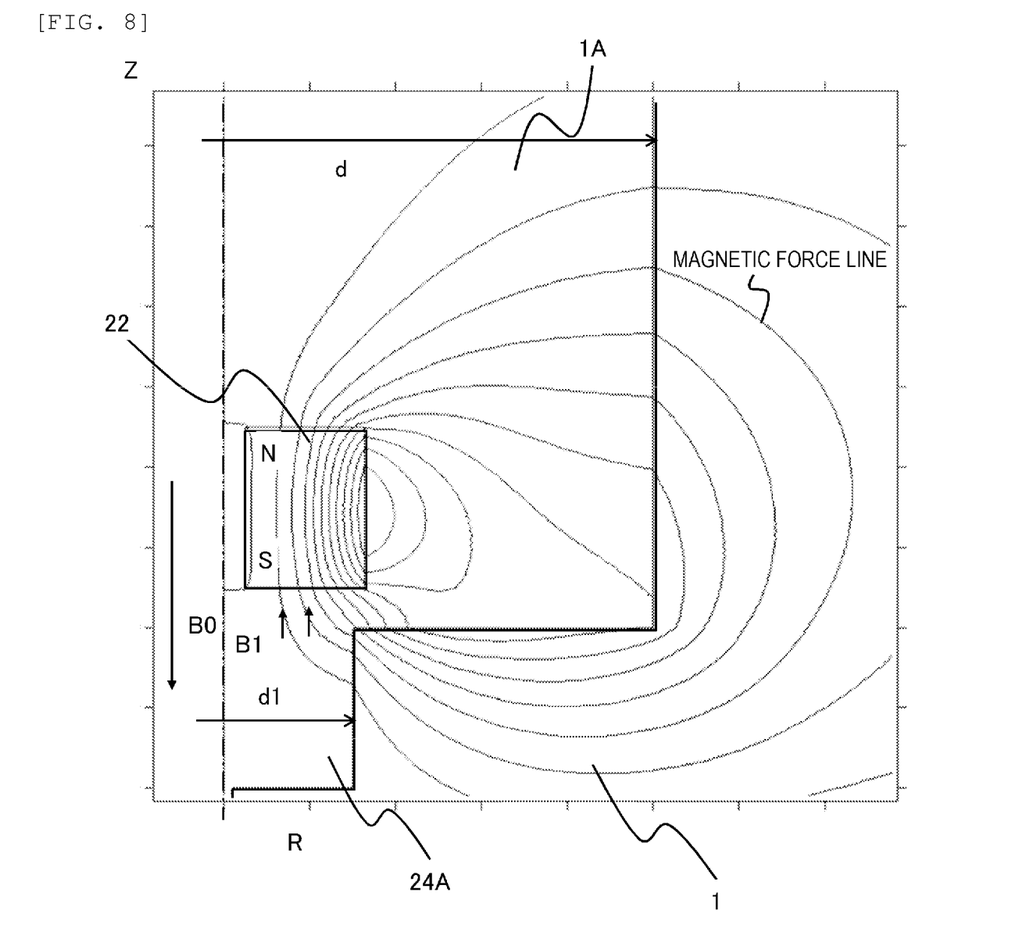
FIG. 8 is a diagram showing magnetic force lines when a magnetic pole shape around the magnetic field generation mechanism in FIG. 4 is changed.
Figure 9:
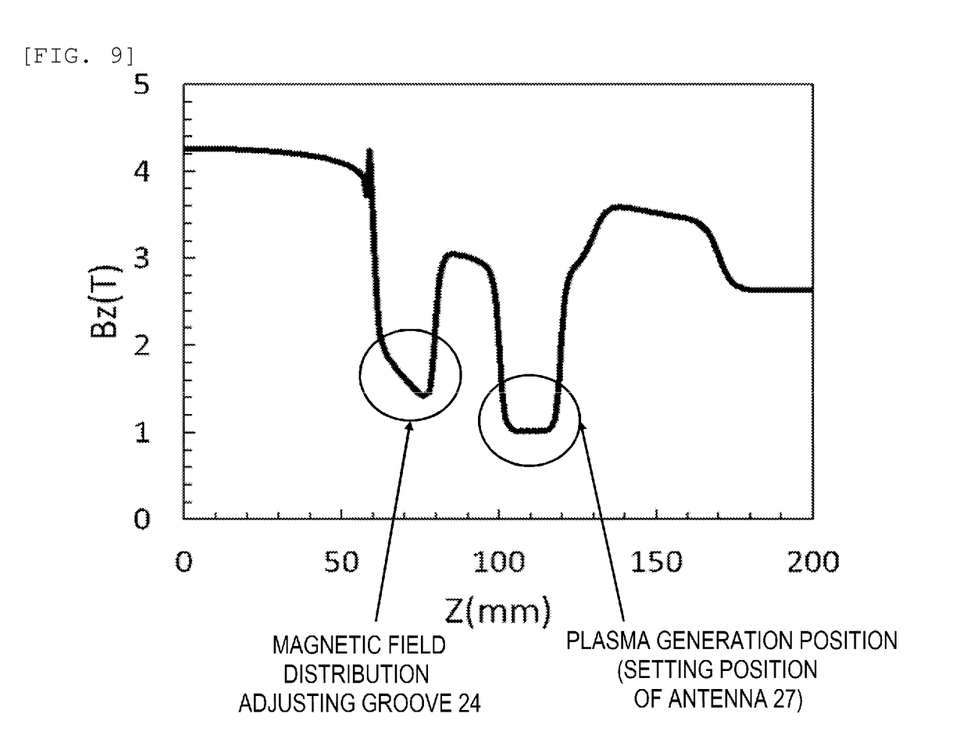
FIG. 9 is a diagram showing a vertical magnetic field distribution at the center of the ion source in FIG. 4.

FIG. 4 is a diagram showing details of the ion source 3 in FIG. 2. FIG. 5 is a diagram showing a magnetic field intensity at a plasma generation position when a diameter d of a hole 1A is changed. FIG. 6 is a diagram showing another example of the ion source 3. FIG. 7 is a diagram showing a relationship between a magnetic field distribution adjusting groove 24 and magnetic force lines generated by a magnetic field generation mechanism 22. FIG. 8 is a diagram showing a relationship between a magnetic field distribution adjusting hole 24A and the magnetic force lines generated by the magnetic field generation mechanism 22. FIG. 9 is a diagram showing an example of a magnetic field distribution generated by the magnetic field generation mechanism 22, a hole diameter d provided in the main magnetic poles 1, and the magnetic field distribution adjusting groove 24.

As shown in FIG. 4, the ion source 3 includes a microwave power supply 25, a radiofrequency waveguide 21, an antenna 27, the magnetic field generation mechanism 22, the magnetic field distribution adjusting groove 24, an internal discharge chamber 23, a sample gas source 30, and a sample gas introduction line 31.

The ion source 3 of the present embodiment is a type of an ion source that accelerates electrons by using microwaves and generates plasma by the accelerated electrons, and is referred to as a microwave ion source or an electron cyclotron resonance (ECR) ion source having a small number of consumables and a long life span.

The microwave power supply 25 is a device that generates a microwave for generating plasma in the internal discharge chamber 23 of the ion source 3, and is provided outside the main magnetic poles 1 as shown in FIG. 4.

The microwave is generated by the microwave power supply 25 and introduced into the internal discharge chamber 23 by the antenna 27 through an internal conductor 26 in the radiofrequency waveguide 21 filled with an insulator 20.

The sample gas source 30 is a supply source of a sample gas for generating the plasma, which is a supply source of the ions to be accelerated by the accelerator 50, and is, for example, a hydrogen gas cylinder when the ions to be accelerated are protons. In the invention, the sample gas to be introduced into the internal discharge chamber 23 is not limited to a hydrogen gas, and there is not particularly limitation on the sample gas.

The sample gas introduction line 31 is a pipe for feeding the sample gas from the sample gas source 30 to the internal discharge chamber 23. The sample gas flowing through the sample gas introduction line 31 can constantly flow, or may be introduced in a pulse shape, and is not particularly limited thereto.

The radiofrequency waveguide 21 is a coaxial cable in which the insulator 20 is filled around the internal conductor 26, and is configured to allow the microwave to transmit from the microwave power supply 25 to the antenna 27. When it is considered that the radiofrequency waveguide 21 is inserted to a center portion of the main magnetic poles 1, the radiofrequency waveguide 21 is preferably formed of a cable whose outer side is covered with a metal and which is not easily deformed, and a normal coaxial cable may be used.

The insulator 20 prevents the plasma from being generated during the microwave transmission and prevents abnormal discharge in a transmission region. The insulator 20 is, for example, polytetrafluoroethylene, alumina, or the like, but is not particularly limited thereto.

The antenna 27 is connected to a terminal end side of the internal conductor 26 of the radiofrequency waveguide 21, and has a structure protruding into the internal discharge chamber 23.

The radiofrequency waveguide 21 and the antenna 27 constitute a waveguide for introducing the microwave generated by the microwave power supply 25 to a region to which the magnetic field generated by the main magnetic poles 1 is applied.

When surfaces of the antenna 27 and the internal discharge chamber 23 are coated with an insulator, damage from the plasma can be further reduced. Examples of the insulator include boron nitride, and the like. In addition, an area to be insulated may be an entire surface or a part thereof, but it is desirable to coat the entire surface in order to exhibit effects to the maximum extent.

The antenna 27 may have a cylindrical shape using the internal conductor 26 as it is, or may be formed of a conductor separately connected to the internal conductor 26, a shape thereof is not particularly limited, and may be a circular plate shape, a spiral shape, or the like other than the cylindrical shape.

It is desirable that the internal discharge chamber 23 has a cooling structure to reduce deformation and damage caused by heating of beam plasma. Alternatively, the internal discharge chamber 23 may be made of a heat-resistant material, and cooling may be omitted. For example, the internal discharge chamber 23 is made of molybdenum, carbon, copper, or the like.

In addition, a hole 23A for extraction is provided in a side surface of the internal discharge chamber 23, and an extraction beam 15 is obtained from the hole 23A by a radiofrequency electric field of the radiofrequency acceleration electrode 7. A structure for generating the extraction beam 15 and provided on the side surface of the internal discharge chamber 23 is not limited to the hole 23A, and a slit or the like can be used.

In the ion source 3 of the present embodiment, a microwave electric field E is generated between the antenna 27 and the internal discharge chamber 23 by the microwave introduced by the radiofrequency waveguide 21 and the antenna 27.

In order to generate the plasma by the microwave, an electric field and a magnetic field orthogonal to the electric field are required. A magnetic field intensity of the main magnetic field B0 of the magnetic pole gap G generated by the main magnetic poles 1 is, for example, 2 to 9 tesla. The microwave generates the plasma by utilizing resonance motion (spiral motion) of electrons due to the electric field and the magnetic field.

Here, a resonance frequency is determined by the magnetic field intensity and a frequency of the microwave, and for example, in a magnetic field of 9 tesla (T), the resonance frequency is 250 gigahertz (GHz) or more. There are problems that when the frequency increases, a wavelength becomes shorter and the transmission becomes difficult, and that when a structure of a transmitter becomes complicated, it becomes difficult to increase an output.

For this reason, it is important to lower the resonance frequency in a plasma generation unit, and for this purpose, it is necessary to reduce the magnetic field intensity generated by the main magnetic poles 1 as much as possible.

Therefore, in the present embodiment, the hole 1A also serving for insertion of the ion source 3 is formed in the main magnetic poles 1, and the magnetic field intensity at a plasma generation position of the ion source 3 is reduced depending on a size of the hole diameter d.

FIG. 5 shows the magnetic field intensity at the plasma generation position when the hole diameter d is changed. As shown in FIG. 5, it can be seen that the magnetic field intensity is reduced when the hole diameter of the hole 1A of the main magnetic poles 1 increases. However, as shown in FIG. 5, when the diameter d of the hole 1A is 400 millimeters (mm) or more, the magnetic field can be further reduced, but the magnetic field intensity of the magnetic pole gap G rapidly decreases. Therefore, an upper limit of the hole diameter of the hole 1A is preferably 400 millimeters (mm).

It is considered that the size of the hole diameter d at which the magnetic field of the gap G starts to decrease changes depending on a material of the main magnetic poles 1 and a size of the magnetic pole gap G. The range shown in FIG. 5 is an example, and is not particularly limited to this value.

Since there is a limit to effects of reducing the magnetic field intensity by the hole 1A as described above, in the invention, in order to further reduce the main magnetic field B0, the magnetic field generation mechanism 22 that generates a magnetic field in a direction opposite to that of the magnetic field generated by the main magnetic poles 1 is provided inside the hole 1A provided in a part of the main magnetic poles 1. The magnetic field generation mechanism 22 generates the magnetic field in the direction opposite to a direction of the main magnetic field B0, and reduces the magnetic field in a canceling manner.

The magnetic field generation mechanism 22 is formed of, for example, a permanent magnet as shown in FIG. 4, but can also be formed of a coil 22A as shown in FIG. 6. When the magnetic field generation mechanism 22 is formed of the coil 22A as shown in FIG. 6, a magnetic field distribution that cancels the main magnetic field can be adjusted.

The magnetic field generation mechanism 22 or the coil 22A may be provided on an entire inner peripheral surface of the hole 1A or may be provided on a part of the inner peripheral surface of the hole 1A, and may be provided as long as the magnetic field in the direction opposite to that of the main magnetic field generated by the main magnetic poles 1 can be generated.

As shown in FIG. 7, a magnetic field B1 in a direction opposite to the direction of the main magnetic field B0 is generated by the magnetic field generation mechanism 22. Accordingly, as shown in FIG. 4, a final magnetic field B0' is generated. The plasma is generated in the internal discharge chamber 23 inside the main magnetic poles 1 by the magnetic field B0' and the introduced microwave.

Further, as shown in FIG. 4, the magnetic field intensity generated by the main magnetic poles 1 can be further reduced by the magnetic field distribution adjusting groove 24 provided between the magnetic field generation mechanism 22 and a magnetic pole facing surface of the main magnetic poles 1.

The magnetic field distribution adjusting groove 24 has a groove shape having a rectangular cross section as shown in FIG. 7, and is not limited to this shape. In addition to the groove, as shown in FIG. 8, the magnetic field distribution adjusting hole 24A having a diameter dl smaller than the hole diameter d of the hole 1A may be used. Further, a plurality of hole diameters may be used.

When the magnetic field distribution adjusting groove 24 is to be formed, the magnetic field distribution adjusting groove 24 may be formed by cutting an inner peripheral surface side of the hole 1A of the main magnetic poles 1, or may be formed by forming a hole such as the magnetic field distribution adjusting hole 24A and then attaching a circular plate member made of the same material as the main magnetic poles 1 to an opening periphery of a position of the hole by welding or the like, and the invention is not particularly limited thereto.

As shown in FIG. 9, the magnetic field distribution adjusting groove 24 reduces the magnetic field from 4.2 tesla (T) to 1 tesla at a center position at the plasma generation position. The resonance frequency at this time is 28 gigahertz (GHz), and the standard microwave power supply 25 and the radiofrequency waveguide can be used. By increasing the magnetic field intensity generated by the magnetic field generation mechanism 22, the magnetic field B0' can be further reduced, and the resonance frequency can also be reduced.

In the present embodiment, as shown in FIGS. 2 and 4, the internal discharge chamber 23 of the ion source 3 is disposed inside the main magnetic poles 1, and the extraction beam 15 is obtained from the plasma generated by the ion source 3 by the radiofrequency electric field generated by the high frequency acceleration electrode 7 by the radiofrequency power supply 16.

The extracted extraction beam 15 is accelerated to predetermined energy while drawing the closed orbit 9 by effects of the main magnetic field B0 formed by the convex magnetic pole and the electric field of the radiofrequency acceleration electrode 7, and then extracted from the closed orbit 9 and output to the outside of the main magnetic poles 1.

Next, effects of the present embodiment will be described.

The particle beam therapy system 100 according to the above present embodiment includes: the accelerator 50 including the main magnetic poles 1 facing to each other, the radiofrequency acceleration electrode 7, and the ion source 3; the irradiation nozzle 54 configured to perform irradiation with the charged particle beam accelerated by the accelerator 50; the beam transport system 52 configured to transport the charged particle beam to the irradiation nozzle 54; and the couch 40 on which the patient 45 to be irradiated with the charged particle beam is placed. The ion source 3 among these includes the microwave power supply 25 provided outside the main magnetic poles 1, the radiofrequency waveguide and the antenna 27 configured to introduce the microwave generated by the microwave power supply 25 to the region to which the magnetic field generated by the main magnetic poles 1 is applied, and a magnetic field generation unit provided inside the hole 1A provided in a part of the main magnetic poles 1 and configured to generate the magnetic field in the direction opposite to that of the magnetic field generated by the main magnetic poles 1. The plasma is generated inside the main magnetic poles 1 by the magnetic field generated by applying the magnetic field generated by the magnetic field generation unit in the opposite direction to the main magnetic field decreased according to the diameter of the hole 1A and the microwave introduced by the radiofrequency waveguide 21 and the antenna 27.

With such a configuration, since the plasma can be generated inside the main magnetic poles 1 even when there is no filament in the ion source 3, it is possible to obtain the ion source 3 having a long life span without damage of the filament as in an internal ion source of related art described in PTL 1, which is a built-in ion source. In addition, since the structure of the ion source 3 is simple and the assembly and disassembly are easy, a maintenance time is shortened, and an effect of improving an operation rate of the apparatus is also obtained along with an increase in a life span of the ion source.

Since the internal ion source in which the filament is not used can be configured as described above, by using the ion source having a long life span without a damaged portion to configure a circular accelerator, it is possible to provide a circular accelerator that achieves a long life span and a high operation rate and to provide a particle beam therapy system using the same.

Since a magnetic field reduction structure is provided on the inner peripheral surface side of the hole 1A and is provided on the inner side of the main magnetic poles 1 with respect to the magnetic field generation unit, it is possible to obtain effects such as cost reduction in the microwave power supply 25 and the like and improvement in plasma generation efficiency.

Further, since the magnetic field generation unit is formed of the permanent magnet or the coil 22A, it is possible to reduce the magnetic field intensity formed by the main magnetic poles 1 with a simple structure.

In addition, since the magnetic field reduction structure is formed of the magnetic field distribution adjusting groove 24 or the magnetic field distribution adjusting hole 24A having a smaller diameter than the hole 1A, it is possible to more effectively reduce the magnetic field intensity formed by the main magnetic poles 1 with a simple structure, and it is possible to more easily obtain the effects such as the cost reduction in the microwave power supply 25 and the like and the improvement in the plasma generation efficiency.

Other Embodiments

The invention is not limited to the embodiments described above, and includes various modifications. For example, the above-descried embodiments are described in detail for easy understanding of the invention, and the invention is not necessarily limited to those including all the configurations described above.

For example, as the accelerator 50, a synchrocyclotron accelerator that modulates an acceleration frequency can be used instead of the cyclotron accelerator having uneven magnetic poles as described above.

The synchrocyclotron accelerator is one type of accelerators in which a cyclotron is improved, and repeatedly accelerates by applying a radiofrequency electric field to charged particles that perform circular motion between large magnetic poles. In addition, at a high speed, a mass of the accelerated particles increases due to the relative theoretical effect, and a cycle of the circular motion of the charged particles in the magnetic field increases in proportion to the mass. Deviation of the cycle and a radiofrequency voltage caused by the increase is eliminated by modulating a frequency.

Since the synchrocyclotron accelerator has the same configuration as the cyclotron accelerator, the ion source 3 can be disposed in the main magnetic poles 1, and the same effect can be obtained.

In addition, the accelerator 50 may be an accelerator of an eccentric orbit type having an aggregation region in which an orbit of the closed orbit of the beam on a high energy side is densely gathered on an extraction region side to the outside of the accelerator 50.

REFERENCE SIGN LIST 1 main magnetic pole
1A hole
2 annular coil
3 ion source
6 vacuum vessel
7 radiofrequency acceleration electrode
9 closed orbit
10 convex magnetic pole
15 extraction beam
16 radiofrequency power supply
20 insulator
21 radiofrequency waveguide (waveguide)
22 magnetic field generation mechanism (magnetic field generation unit)
22A coil 23 internal discharge chamber
23A hole
24 magnetic field distribution adjusting groove (magnetic field reduction structure)
24A magnetic field distribution adjusting hole (magnetic field reduction structure)
25 microwave power supply (microwave emission source)
26 internal conductor
27 antenna (waveguide)
30 sample gas source
31 sample gas introduction line
40 couch
45 patient (target)
50 accelerator
52 beam transport system
54 irradiation nozzle
56 control device
100 particle beam therapy system

The invention claimed is:

1. An ion source used for a circular accelerator including magnetic poles facing to each other, and a radiofrequency acceleration electrode, the ion source comprising:
    a microwave emission source provided outside the magnetic poles;
    a waveguide configured to introduce a microwave emitted from the microwave emission source to a region to which a main magnetic field generated by the magnetic poles is applied; and
    a magnetic field generation unit provided inside a hole provided in a part of the magnetic poles and configured to generate a magnetic field in a direction opposite to a direction of the magnetic field generated by the magnetic poles, wherein
    plasma is generated inside the magnetic poles by a magnetic field generated by applying the magnetic field generated by the magnetic field generation unit in the opposite direction to the main magnetic field decreased according to a diameter of the hole and the microwave introduced by the waveguide.

2. The ion source according to claim 1, further comprising:
    a magnetic field reduction structure provided on an inner peripheral surface side of the hole and provided on an inner side of the magnetic poles with respect to the magnetic field generation unit.

3. The ion source according to claim 1, wherein
    the magnetic field generation unit is formed of a permanent magnet or a coil.

4. The ion source according to claim 2, wherein
    the magnetic field reduction structure is formed of a groove or a hole having a diameter smaller than that of the hole.

5. A circular accelerator comprising:
    the ion source according to claim 1.

6. A particle beam therapy system comprising:
    the circular accelerator according to claim 5;
    an irradiation nozzle configured to perform irradiation with a charged particle beam accelerated by the circular accelerator;
    a beam transport system configured to transport the charged particle beam to the irradiation nozzle; and
    a couch on which an irradiation target to be irradiated with the charged particle beam is placed.

* * * * *